United States Patent
Henderson et al.

(10) Patent No.: US 11,419,848 B2
(45) Date of Patent: *Aug. 23, 2022

(54) COMBINATION OF UNSAPONIFIABLE LIPIDS COMBINED WITH POLYPHENOLS AND/OR CATECHINS FOR THE PROTECTION, TREATMENT AND REPAIR OF CARTILAGE IN JOINTS OF HUMANS AND ANIMALS

(71) Applicant: NUTRAMAX LABORATORIES, INC., Lancaster, SC (US)

(72) Inventors: Todd R. Henderson, Edgewood, MD (US); Louis Lippiello, Forest Hill, MD (US); Charles Filburn, Forest Hill, MD (US); David Griffin, Lancaster, SC (US)

(73) Assignee: NUTRAMAX LABORATORIES, INC., Lancaster, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/997,233

(22) Filed: Aug. 19, 2020

(65) Prior Publication Data

US 2020/0375941 A1 Dec. 3, 2020

Related U.S. Application Data

(60) Continuation of application No. 16/507,278, filed on Jul. 10, 2019, now Pat. No. 10,780,077, which is a continuation of application No. 15/433,281, filed on Feb. 15, 2017, now Pat. No. 10,456,372, which is a continuation of application No. 14/296,031, filed on Jun. 4, 2014, now Pat. No. 9,572,791, which is a continuation of application No. 12/780,642, filed on May 14, 2010, now Pat. No. 8,808,770, which is a division of application No. 11/889,060, filed on Aug. 8, 2007, now abandoned, which is a continuation of application No. 11/192,362, filed on Jul. 29, 2005, now abandoned.

(60) Provisional application No. 60/592,322, filed on Jul. 30, 2004.

(51) Int. Cl.
| | |
|---|---|
| *A61K 36/00* | (2006.01) |
| *A61K 31/353* | (2006.01) |
| *A61K 31/05* | (2006.01) |
| *A61K 36/48* | (2006.01) |
| *A61K 36/82* | (2006.01) |
| *A61K 31/685* | (2006.01) |
| *A61K 36/54* | (2006.01) |
| *A61K 9/00* | (2006.01) |

(52) U.S. Cl.
CPC .......... *A61K 31/353* (2013.01); *A61K 9/0053* (2013.01); *A61K 31/05* (2013.01); *A61K 31/685* (2013.01); *A61K 36/48* (2013.01); *A61K 36/54* (2013.01); *A61K 36/82* (2013.01)

(58) Field of Classification Search
CPC .......... A61K 2236/37; A61K 2236/333; A61K 31/05

See application file for complete search history.

(56) References Cited

U.S. PATENT DOCUMENTS

| | | | | |
|---|---|---|---|---|
| 6,428,817 | B1 * | 8/2002 | Collin | A61K 9/0056 424/439 |
| 2003/0129261 | A1 * | 7/2003 | Henderson | A61K 31/00 424/757 |
| 2003/0224071 | A1 * | 12/2003 | Murad | A61K 8/19 424/728 |

* cited by examiner

*Primary Examiner* — Qiuwen Mi
(74) *Attorney, Agent, or Firm* — Dickinson Wright PLLC; Andrew D. Dorisio

(57) ABSTRACT

The present invention relates to a composition for the protection, treatment and repair of cartilage in humans and animal joints. The composition contains a combination of unsaponifiable lipids together with one or more of polyphenols and/or catechins. The composition or kit may contain avocado:soybean unsaponifiables (ASU) and green tea.

9 Claims, No Drawings

COMBINATION OF UNSAPONIFIABLE LIPIDS COMBINED WITH POLYPHENOLS AND/OR CATECHINS FOR THE PROTECTION, TREATMENT AND REPAIR OF CARTILAGE IN JOINTS OF HUMANS AND ANIMALS

RELATED APPLICATIONS

This application is a continuation application of U.S. patent application Ser. No. 16/507,278, filed Jul. 20, 2019, which is a continuation application of U.S. patent application Ser. No. 15/433,281, filed Feb. 15, 2017, now U.S. Pat. No. 10,456,372, which is a continuation of U.S. patent application Ser. No. 14/296,031, filed Jun. 4, 2014, now U.S. Pat. No. 9,572,791, which is a continuation application of U.S. patent application Ser. No. 12/780,642, filed May 14, 2010, now U.S. Pat. No. 8,808,770, which is a divisional application of U.S. patent application Ser. No. 11/889,060, filed Aug. 8, 2007, which is a continuation application of U.S. patent application Ser. No. 11/192,362, filed Jul. 29, 2005, which claims the benefit of U.S. Provisional Patent Application No. 60/592,322, filed on Jul. 30, 2004, the contents of all of which are incorporated herein by reference.

FIELD OF THE INVENTION

The present invention relates to a composition for the protection, treatment and repair of cartilage in humans and animal joints.

BACKGROUND OF THE INVENTION

Degenerative joint disease (DJD) results from the cumulative effects of an imbalance between synthesis and degradation of components of cartilage extracellular matrix. This imbalance is associated with disregulated activity of inflammatory cytokines and production of prostaglandins that mediate pain. Progression of the disorder occurs when this imbalance persists. Agents that act to increase synthesis of cartilage components and suppress the activity of specific cytokines, particularly of interleukin-1-beta (IL-1-$\beta$) and tumor necrosis factor alpha (TNF-$\alpha$), have the potential to relieve symptoms of DJD and stop its progression. Both of these cytokines act through mechanisms that involve generation of reactive oxygen species (ROS) and reactive nitrogen species (RNS) that lead to suppression of synthesis of cartilage matrix proteoglycans along with increased production of prostaglandins, nitric oxide, and activation of metalloproteinases that degrade cartilage proteins. A combination of agents that is capable of interacting with these mechanisms in different ways and to stimulate the anabolic response needed in chondrocytes for maintenance and/or restoration of matrix components could be effective in the protection, treatment and repair of connective tissue.

Polyphenols and Catechins

Various polyphenols can be sourced from berries and other fruits. Catechins are found primarily in teas. The preferred source of polyphenols and catechins are sourced from green tea. Green tea contains a mixture of catechins, including epicatechin (EC), epigallocatechin (EGC), epicatechin gallate (ECG) and epigallocatechin gallate (EGCG). These catechins have potent antioxidant activity, acting as scavengers of the free radicals (ROS and RNS) involved in damage to cells. They also act by chelating metals that catalyze production of ROS (1). This antioxidant activity may interfere with the damaging effects of agents, e.g. fibronectin fragments (Fn-f) and cytokines, that can cause DJD. Antioxidants block the effects of Fn-f, which include increased expression and activity of both cytokines IL-1 and TNF-$\alpha$ (2,3). In addition, recent studies have shown that green tea polyphenols significantly reduce the incidence of collagen-induced arthritis in mice that was associated with reduced expression of TNF-$\alpha$ and cyclooxygenase 2, a TNF-$\alpha$ regulated enzyme that catalyzes the production of prostaglandin E2 (4). Other studies have shown that the EGCG in green tea inhibits IL-1 induced expression of nitric oxide synthase and nitric oxide production and suppresses activation of nuclear factor-kB, a key step in initiation of the cytokine effects (5). Furthermore, the catechins in green tea were recently shown to potently inhibit aggrecanase activities known to be involved in the early stages of destruction of cartilage proteoglycans (6). Thus, the components of green tea have the potential to ameliorate the cause and the symptoms of DJD through multiple mechanisms. The green tea may be administered as an extract or standardized to polyphenols or catechins.

Unsaponifiable Lipids

Vegetable oils, including coconut, peanut and safflower oil to name a few, are possible components of the human diet that contain an important class of compounds termed unsaponifiable lipids. One rich source of unsaponifiable lipids are avocados and soybean oil, with avocado having approximately four times more lipids than those found in other commonly eaten fruits. Many of the health benefits of soy, widely used as a staple food in Asian countries, may be due to this unsaponifiable fraction which also includes isoflavones. Unsaponifiable lipids are defined as the material which does not react with basic agents to form soaps. Included in this class are phytosterols, fat soluble vitamins A, D, E and K, bioflavinoids, phytoestrogens and small organic molecules called terpenes. The major components by weight of the unsaponifiable lipid fraction are a group of compounds called phytosterols which differ slightly in structure and include beta sitosterol, campesterol and stigmasterol. Of the many beneficial actions attributed to phytosterols, their ability to reduce pain, swelling, and tissue injury in joints is proposed. With aging and stress, increased amounts of phytosterols are thought to be necessary to maintain normal biological functions (1,2).

Biological Activity

Phytosterols have potent biological activities, some of which reduce the joint pain and swelling characteristic of inflammatory joint disorders as well as symptoms characteristic of trauma or aging related joint disorders. In addition, these agents beneficially alter the body's immune response in a fashion which helps to minimize joint tissue destruction attributed to an allergic tissue reaction. Studies indicate phytosterols are active in immune modulation (3) and have anti-inflammatory and antipyretic activity (4). Most of these activities are a result of the effect of phytosterols inhibiting the production by inflammatory cells of chemical agents (cytokines) which cause tissue damage and stimulation of anabolic activity of chondrocytes. Avocado/soybean oil unsaponifiables (ASU) is a preferred source of unsaponifiable lipids for the protection, treatment and repair of connective tissue conditions.

In Vitro Tests

Prior researchers have conducted in vitro tests on ASU. The in vitro model previously used to test ASU is based on monitoring reduction of interleukin-1 (IL-1)-induced metalloprotease activity, nitric oxide or prostaglandin synthesis (all agents associated with cartilage degradation, tissue inflammation, or pain) (5-9). ASU was shown to inhibit the action of IL-1 at doses of 1 to 10 ug/ml. A combination of 2:1 soy:avocado was found to be even more effective than either agent alone (5,8). It was also noticed that this mixture was the main combination that was effective in decreasing production of collagenolytic activity (9). Fibroblasts also appear to be responsive to ASU. Metalloprotease activity (MMP-2 and MMP-3) was inhibited at low doses of ASU and at higher doses the tissue-inhibitors of metalloproteases was increased (7). The above mentioned assays could be related to the beneficial physiological (symptomatic relief) effects. Other indices tested relate to a possible increase capacity for repair and regeneration of articular cartilage. For example, the anticatabolic activity of ASU was shown to be paired with a direct effect of ASU on stimulating collagen and proteoglycan production, possibly by increasing transforming growth factor-beta 1 and 2 synthesis (6). Research in our laboratory also has shown that ASU is effective in improving cartilage synthesis in-vitro.

In Vivo Tests in Animals

Prior researchers have conducted in vivo animal tests on ASU. An increase in collagen synthesis was observed in a carrageenan induced granuloma in the "Hairless" rat following 15 days of percutaneously applied ASU (10). Mice that had subcutaneous implantation of rat articular cartilage wrapped in cotton were treated orally for 2 weeks with the unsaponifiable fraction of either ASU, avocado alone or soybean alone daily for 2 weeks (13 mg/kg avocado or 26 mg/kg soya or both in a ratio of 1:2 at a dose of 39 mg/kg). Parameters measured included proteoglycans and hydroxyproline content of the cartilage. Results indicate that unsaponifiables of both avocado and soybean reduced the degeneration of proteoglycans and hydroxyproline content of the implanted cartilage that was induced by the granuloma tissue. A greater effect was seen using a combination of avocado and soybean, an effect which was dose dependent (11).

A third more pertinent study involved oral administration of ASU (900 mg/weekday) to meniscectomized sheep for 3 and 6 months (12). In this model a "subtle but statistically significant protective effect on articular cartilage" was noted from computerized image analysis of histological stained cartilage.

Many plants contain similar type agents generally classified as unsaponifiable lipids. Potent anti-inflammatory activity has also been associated with these sources. For example, Park et al (13) found anti-inflammatory activity in an ethanolic extract of cactus which was identified as beta sitosterol. Using the carrageenan paw oedema model in rats, beta sitosterol was found to be one of the potent anti-inflammatory agents in extracts of Verbena officinalis (14). The isolated sterols stigmasterol and beta sitosterol were potent anti-inflammatory agents when administered topically and in a chronic inflammation model in the mouse (15). A sterol fraction containing 7.6% campesterol, 28.4% stigmasterol and 61.1% beta sitosterol demonstrated anti-inflammatory activity in the carrageenan paw oedema model in mice after oral administration of 30 and 60 mg/kg (16).

In Vivo Tests In Humans

Prior researchers have conducted in vivo tests in humans on ASU. Individuals with primary femorotibial or hip OA of at least six months duration were dosed with 300 mg of a 2:1 avocado:soybean unsaponifiable preparation for 3 months. Indices measured included NSAID intake, Lequesne's index and physician visual analog scale for pain and functional index. All indices showed improvement at p<0.01 or better (17). In a double-blind study, individuals with knee OA (femoro-tibial) were dosed with 300 or 600 mg of an avocado:soybean unsaponifiable for three months. Indices measured included NSAID and analgesic intake between day 30 and day 90. All indices improved with treatment at p<0.01 or better with NSAID intake decreasing by more than 50% in 71% of the individuals compared to 36% in individuals receiving placebo. Lequesne's index dropped by 3.9 and 2.9 points in ASU 300 and 600 mg respectively against 1.6 in placebo. Similar results were observed in individuals given 300 or 600 mg (18). Eighty-five out of 164 individuals with painful primary OA of the knee or hip were dosed for 6 months with 300 mg unsaponifiables after a 15 day washout period for NSAIDs.

Efficacy was determined by Lequesne's functional index, visual analog pain scale, intake of NSAIDs and overall disability score. Pain decreased from a score of 56.1 to 35.3 in the ASU group and from 56.1 to 45.7 in the placebo group (p<0.003). Values for NSAID intake showed consumption lower in ASU group (48% versus 63%). Lequesne's test score decreased from 9.7 to 6.8 in the ASU group and from 9.4 to 8.9 in the placebo group. The overall success rate was 39% in the ASU group and 18% in the placebo group. Improvement was more marked in individuals with hip OA and a residual effect was observed at month eight (19).

One hundred sixty-three individuals in this pilot 2 year study evaluating structural changes in the hip joint. Individuals with painful primary OA of hip and joint space > or = to 1 mm. (Kellgren grade 1 to 3) with at least a 6 month history of pain and AFI index > or = to 4. Primary assessment was decrease in joint space width performed in standing, position. Results indicate a failure to demonstrate significant reduction in progression of joint space loss compared to placebo. ASU did reduce progression of joint space loss (20).

Rationale

We believe that polyphenols and catechins, especially from green tea, together with unsaponifiable lipids, especially from ASU, can have beneficial effects on the biochemical processes that underlie development and/or progression of DJD. In our invention, by "green tea" we mean green tea available as a tea, as well as green tea available as an extract, such as in a powder form. The antioxidant activity of components of green tea have the capacity to attack the free radicals known to be involved in disregulated cytokine activity in osteoarthritis. The additional capacity to inhibit specific proteases involved in cartilage degradation provides an additional mechanism for combating DJD. The anti-inflammatory activity of avocado and soybean unsaponifiables can also attack cytokine signaling, but apparently by less understood mechanisms. They also provide direct anabolic activity that is needed to restore the balance between anabolic and catabolic activity. A combination of unsaponifiable lipids with one or more of polyphenols or catechins should work well together. Thus the present invention consists of a combination of these agents over a range of doses.

Dosage Ranges and Preferred Sources

Polyphenols/catechins: about 3 mg to about 10 grams, with the preferred source of polyphenols being green tea. The green tea may be combined with phosphatidylcholine to improve absorption.

Unsaponifiable lipids: about 5 mg to about 12 grams, with the preferred source being ASU.

EXAMPLES

The following examples are merely illustrative of the present invention and are not to be considered as limiting the invention, which is properly delineated in the following claims. Moreover, it should be noted that the use of the present or future tense in these examples is reflective of the fact that the examples are prophetic. MPEP ¶608.01(p).

Example 1

A 70 kg 60 year old man has knee joint pain and radiologically diagnosed degenerative joint disorder. Intake on a daily basis of a supplement that contains 100 mg green tea extract and 300 mg avocado-soybean unsaponifiables reduces these symptoms.

Example 2

A 20 kg 6 year old Labrador retriever has degenerative joint disorder localized to the hip and has difficulty rising and ascending stairs. Intake on a daily basis of a supplement containing 20 mg green tea extract and 30 mg avocado-soybean unsaponifiables reduces these symptoms.

Example 3

A 5 kg cat is diagnosed with spinal arthritis and cannot jump on the windowsill. The cat is administered 3 mg of polyphenols and catechins and 5 mg avocado soybean unsaponifiables. The cat improves dramatically and is now capable of jumping on the windowsill.

Example 4

A 1000 kg horse is diagnosed with bone spavin and treated with 3 grams of epigallocatechin gallate and 4 grams of ASU. The horse responds dramatically.

REFERENCES FOR GREEN TEA

1. Higdon, J. V. and Frei B., Tea Catechins and Polyphenols: Health Effects, Metabolism, and Antioxidant Functions. Critical Reviews in Food Science and Nutrition 4389-143, 2003.
2. Homandberg, G. A. and Wen F. H-Fibronectin Fragment Mediated Cartilage Chondrolysis. J. Suppression by Antioxidants. Biochimica Biophysica Acta 1317:134-142, 1996.
3. Homandberg, G. A., Hui F., Wen C., Purple C., Bewsey K., Koepp H., Huch K. and Harris A. Fibronectin-Fragment-Induced Cartilage Chondrolysis is Associated with Release of Catabolic Cytokines. Biochemical Journal 321:751-757, 1997.
4. Haqqi T, Anthony D. D., Gupta S., Ahmad N., Lee M. S., Kumar G. K. and Mukhtar H. Prevention of Collagen-induced Arthritis in Mice by a Polyphenolic Fraction From Green Tea. Proceedings National Academy Science USA 96:4524-4529, 1999.
5. Singh R., Ahmed S., Islam N., Goldberg V. M. and Haqqi T. M. Epigallocatechin-3-Gallate Inhibits Interleukin-1B-Induced Expression of Nitric Oxide Synthase and Production of Nitric Oxide in Human Chondrocytes. Arthritis & Rheumatism 45:2079-2086, 2002.
6. Vankemmelbeke M. N., Jones, G. C., Fowles C., Ilic M. Z., Handley C. J., Day A. T., Knight C. G., Mort J. S. and Buttle, D., J. Selective inhibition of ADAMTS-1, -4, and -5 by Catechin Gallate Esters. European Journal Biochemistry 270: 2394-2403, 203.

REFERENCES FOR ASU

The following references regarding ASU are herein incorporated by reference in their entirety into this specification.
1. Ling W. H., Jones P. J. H.: Minireview. Dietary Phytosterols: A Review of Metabolism, Benefits and Side Effects. Life Sciences 57: 195-206, 1995.
2. DeJong A., Plat J., Mensink R. P.: Metabolic Effects of Plant Sterols and Stanols (Review). J Nutri Biochem 14: 362-369, 2003.
3. Bouic P. J.: The Role of Phytosterols and Phytosterolins in Immune Modulation: A Review of the Past 10 Years. Curr Opin Clin Nutr Metab Care 4: 471-475, 2001.
4. Gupta M. B., Nath R., Srivastava N., Shanker K., Kishor K., Bhargava K. P.: Antiinflammatory and Antipyretic Activities of Beta Sitosterol. Planta Med 39: 157-163, 1980.
5. Henrotin Y. E., Labasse A. H., Jaspar J. M., DeGroote D. D., Zheng S. X., Guillou G. B., Reginster J. Y.: Effects of Three Avocado/Soybean Unsaponifiable Mixtures on Metalloproteinasses, Cytokines and PGE2 Production by Human Articular Chondrocytes. Clin Rheumatol 17: 31-39, 1998.
6. Boumediene K., Felisaz N., Bogdanowiez P., Galera P., Guillou G. B., Pujol J. P.: Avocado/Soya Unsaponifiabies Enhance the Expression of Transforming Growth Factor Beta I and Beta 2 in Cultured Articular Chondrocyctes. Arthritis Rheum 42: 148-156,1999.
7. Kut-Lasserre C., Miller C. C., Ejeil A. L., Gogly B., Dridi M., Piccardi N., Guillou B., Pellat B., and Godeau. Effect of Avocado and Soybean Unsaponifiables on Gelatinase A (MMP-2), Stromelysin 1 (MMP-3) and Tissue Inhibitors of Matrix Metalloproteinase (TMP-1 and TIMP-2) Secretion by Human Fibroblasts in Culture. J Periodontol 72: 1685-1694, 2001.
8. Henrotin Y. E., Sanchez C., Deberg M. A., et al: Avocado/Soybean Unsaponifiables Increase Aggrecan Synthesis and Reduce Catabolic and Proinflammatory Mediator Production by Human Osteoarthritic Chondrocytes. J Rheumatol 30: 1825-1834, 2003.
9. Mauviel A., Loyau G., Pujol J. P.: Effect of Unsaponifiable Extracts of Avocado and Soybean (Piascledine) on the Collagenolytic Action of Cultures of Human Rheumatoid Synoviocytes and Rabbit Articular Chondrocytes Treated with Interleukin-1. Rev Rhurn Mal Osteoartic 58: 241-245, 1991.
10. Lamaud M. E., Miskulin M., Robert A. M., Wepierre J.: Biochemical Modifications of Connective Tissue Induced by the Non-Saponifiables of Avocado and Soyabean Oils Administered Percutaneously in the Hairless Rat. Pathol Biol 26: 269-274, 1978.
11. Khayyal M. T., El-Ghazaly M. A.: The Possible "Chondroprotective" Effect of the Unsaponifiable Constituents of Avocado and Soya In Vivo. Drugs Exptl Clin Res 24: 41-50, 1998.
12. Cake M. A., Read R. A., Guillou B., Ghosh P.: Modification of Articular Cartilage and Subchondral Bone Pathology in an Ovine Meniscectomy Model of Osteoarthritis by Avocado and Soya Unsaponifiables (ASU). Osteoarthritis & Cartilage 8: 404-411, 2000.
13. Park E. H., Kahng J. H., Lee S. H., Shin K. H.: An Antiinflammatory Principle from Cactus. Fitoterapia 72: 288-290, 2001.
14. Deepak M., Handa S. S.: Antiinflammatory Activity and Chemical Composition of Extracts of Verbena Officinalis. Phytother Res 14: 463-465, 2000.
15. Gomez M. A., Saenz M. T., Garcia M. D., Fernandez M. A.: Study of the Topical Antiinflammatory Activity of Achillea Ageratum on Chronic and Acute Inflammation Models Z Naturforsch [C] 54:937-941, 1999.
16. Navarro A., DeLasHeras B., Villar A.: Antiinflammatory and Immunomodulating Properties of a Sterol Fraction from Sideritis Foetens Chem. Biol Pharm Bull 24: 470-473, 2001.
17. Blotman F., Maheu E., Wuiwik A., Caspard H., Lopez A.: Efficacy and Safety of Avocado/Soybean Unsaponifiables in the Treatment of Symptomatic Osteoarthritis of the Knee and Hip. A Prospective, Multicenter, Three-Month Randomized, Double-Blind, Placebo-Controlled Trial. Rev Rhum Engl Ed 64: 825-834, 1997.
18. Appelboom T., Schuermans J., Verbuggen G., Henrotin Y., Reginster J. Y.: Symptoms Modifying Effect of Avocado/Soybean Unsaponifiables (ASU) in Knee Osteoarthritis. Scand J Rheumatol 30: 242-247, 2001.
19. Maheu E., Mazieres B., Valat J. P., Loyau G., LeLoet X., Bourgeois P., Grouin J. M, Rozenberg S.: Symptomatic Efficacy of Avocado/Soybean Unsaponifiables in the Treatment of Osteoarthritis of the Knee and Hip. Arthritis & Rheum 41:81-91, 1998.
20. Lequesne M., Maheu E., Cadet C., Dreiser R. L.: Structural Effect of Avocado/Soybean Unsaponifiables on Joint Space Loss in Osteoarthritis of the Hip. Arthritis & Rheum 47:50-58, 2002.

What is claimed:

1. A composition comprising at least one of polyphenols and catechins in combination with avocado/soybean unsaponifiables (ASU), formulated for oral administration for the treatment and repair of connective tissue and reduction of inflammation in joints of a human or animal in need thereof, wherein the at least one of polyphenols and catechins in combination with avocado/soybean unsaponifiables (ASU) are provided in synergistically effective amounts.

2. The composition of claim 1, wherein the ASU are in an amount of about 5 mg to about 12 g.

3. The composition of claim 1, wherein the polyphenols and catechins are in an amount of between about 3 mg to about 10 g.

4. The composition of claim 1, wherein the polyphenols and catechins are sourced from one or more of green tea, green tea extract, fruits, and berries.

5. The composition of claim 1, wherein the formulation provides a dose of about 0.04 mg/kg to about 40 mg/kg of green tea extract to the human or animal.

6. The composition of claim 1, wherein the formulation provides a dose of about 0.04 mg/kg to about 4 mg/kg of the polyphenols and catechins to the human or animal.

7. The composition of claim 1, wherein the formulation provides a dose of about 1 mg/kg to about 5 mg/kg of the ASU to the human or animal.

8. The composition of claim 1, further comprising phosphatidylcholine.

9. The composition of claim 1, wherein the ASU and the polyphenols and catechins are in a ratio in the range between 1:2000 and 4000:1.

* * * * *